United States Patent [19]
Axelson, Jr. et al.

[11] Patent Number: 5,860,980
[45] Date of Patent: Jan. 19, 1999

[54] SURGICAL APPARATUS FOR USE IN TOTAL KNEE ARTHROPLASTY AND SURGICAL METHODS FOR USING SAID APPARATUS

[76] Inventors: Stuart L. Axelson, Jr., 12 Churchill Dr., Succasunna, N.J. 07876; James V. Bono, 6 Phillips La., Dover, Mass. 02030; David J. Wartel, 285 Harrington Ave., Lyndhurst, N.J. 07071

[21] Appl. No.: 929,034
[22] Filed: Sep. 15, 1997
[51] Int. Cl.⁶ .................................................. A61B 17/56
[52] U.S. Cl. .................. 606/88; 606/90; 606/96
[58] Field of Search ............... 606/86–90, 102, 606/80, 96; 33/810, 811, 812

[56] References Cited

U.S. PATENT DOCUMENTS

| | | | |
|---|---|---|---|
| 5,116,338 | 5/1992 | Poggie et al. | 606/90 |
| 5,213,112 | 5/1993 | Niwa et al. | 600/587 |
| 5,468,244 | 11/1995 | Attfield et al. | 606/90 |
| 5,597,379 | 1/1997 | Haines et al. | 606/80 |

*Primary Examiner*—Michael Buiz
*Assistant Examiner*—David O. Reip
*Attorney, Agent, or Firm*—Joseph J. Kaliko

[57] ABSTRACT

An apparatus for use in total knee arthroplasty includes a tibia engaging plate which is coupled to an upstanding rack member, a drill bushing bracket coupled to the rack member by a lockable pinion member, and a femoral positioning jig which is rotatably coupled to the drill bushing bracket. The drill bushing bracket has a pair of spaced apart drill bushings which are dimensionally located to correspond in position to medial and lateral condyles of the femur. The centers of the drill bushings lie in a plane which is parallel to the plane in which the tibia engaging plate lies. The femoral positioning jig is provided with a pair of posterior skids, one for the lateral posterior condyle and one for the medial posterior condyle, a pair of holes for attaching the jig to the resected distal femur with spikes, and a pair of holes for receiving the two drill bushings. Two different femoral positioning jigs are provided, one for the right knee and one for the left knee. In both jigs, the hole for receiving the medial drill bushing is circular and the hole for receiving the lateral drill bushing is oblong or kidney shaped. This allows the positioning jig (and the femur) to rotate about the axis of the medial drill bushing. The positioning jigs are also each provided with angular indicia adjacent the lateral oblong hole and the drill bushing bracket is provided with left and right indicia indicating the axial center of each drill bushing.

22 Claims, 5 Drawing Sheets

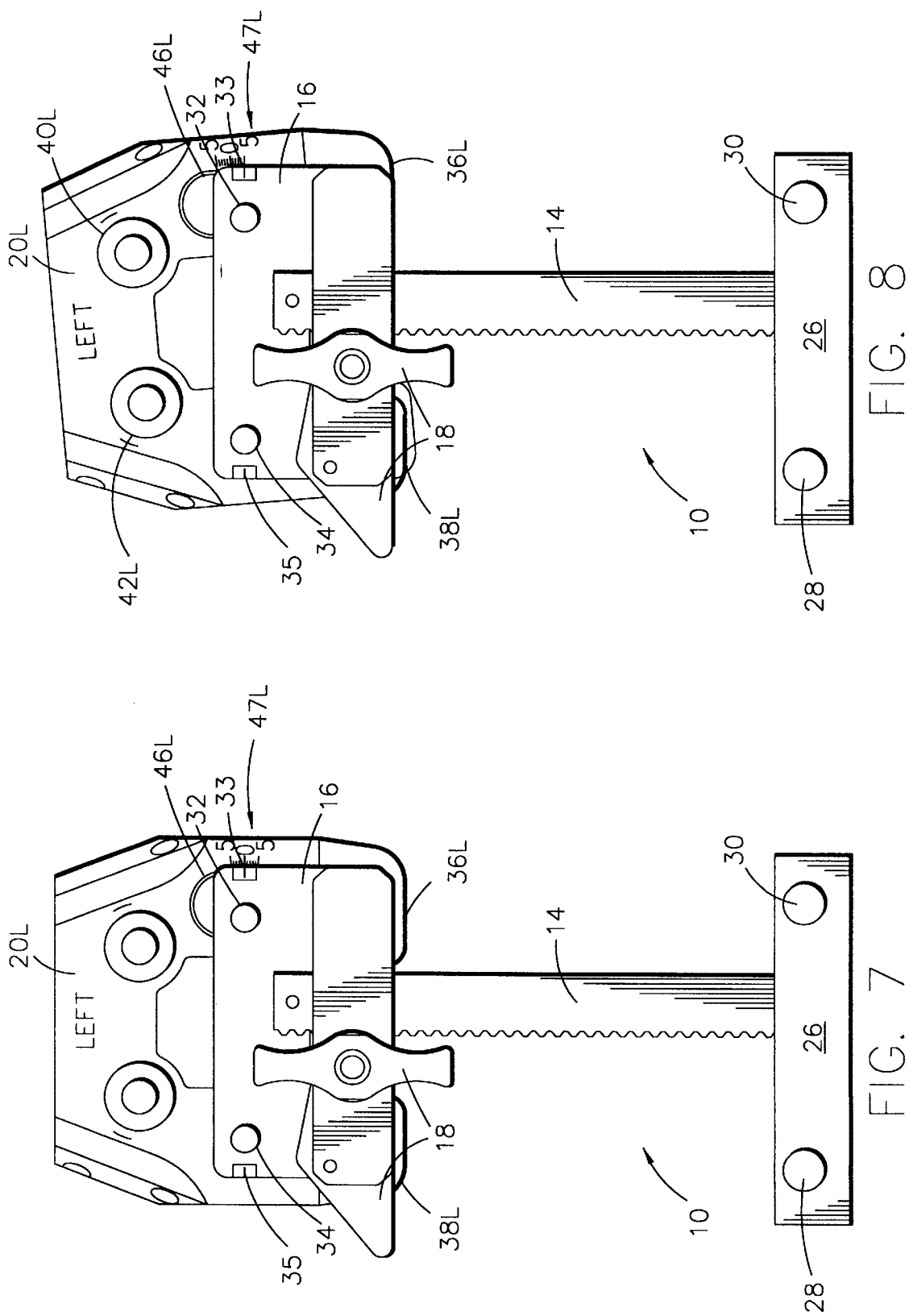

SURGICAL APPARATUS FOR USE IN TOTAL KNEE ARTHROPLASTY AND SURGICAL METHODS FOR USING SAID APPARATUS

BACKGROUND OF THE INVENTION

1. Field of the Invention

The invention relates to surgical apparatus. More particularly, the invention relates to an apparatus for determining the degree of femoral rotation in flexion and for accurately locating a cutting block for resection of the medial and lateral posterior femoral condyles as well as a method for using the apparatus.

2. Description of the Related Art

Total knee arthroplasty involves the replacement of portions of the patellar, femur and tibia with artificial components. In particular, a proximal portion of the tibia and a distal portion of the femur are cut away (resected) and replaced with artificial components. In order to properly place the artificial components, the femur and tibia must be resected in a relatively precise manner so that the artificial knee is balanced throughout its range of motion. Modern knee prostheses are now designed to ensure that so long as the prosthetic knee is balanced in the flexion (90 degrees) and extension (0 degrees) positions, it will function properly throughout its full range of motion.

It is normal for a natural knee to exhibit irregular alignment due to soft tissue differences in the medial and lateral compartments. Differences in the soft tissue, e.g. collateral ligaments, will allow a certain degree of outward (valgus) rotation of the femur relative to the tibia when the knee is in flexion and will allow a certain degree of inward (varus) bending of the tibia and valgus bending of the femur when the knee is in extension. If the artificial knee is not balanced to compensate for these variations in collateral ligaments, it will wear excessively on one condyle, the components may loosen, and most importantly, the patient will experience discomfort.

The traditional methods used to balance the knee relied primarily on x-rays and the surgeon's own senses. Imbalance in the knee when the knee is in extension may be accurately ascertained by x-ray examination. However, imbalance during flexion cannot be ascertained by x-ray examination because the collateral ligaments are contracted during flexion. Traditionally, imbalance during flexion was estimated by visual inspection and palpation of the ligaments during surgery. More recently, various tools referencing bony landmarks have been made available to aid the surgeon in determining the amount of imbalance when the knee is in flexion.

According to an exemplary state of the art procedure, the natural knee is first examined in extension. The potential varus/valgus conditions are assessed with the aid of an x-ray prior to performing the distal femoral and proximal tibial resection. Cutting blocks are attached to the femur and the tibia with drill pins and the proximal tibia and distal femur are resected using either classical or anatomic alignment methods.

The difference in the two alignment approaches is due to a difference in opinion among specialists. The objective of classical alignment is to create a prosthetic joint line which is perpendicular to the reconstructed mechanical axis of the joint. Classical alignment specifies a neutral tibial cut of 0 degrees varus and a valgus femoral cut of 5 degrees–7 degrees. The objective of anatomic alignment is to reproduce a joint line which is parallel to the ground with a normal gait pattern. Anatomic alignment specifies a tibial cut which is made in a plane having a varus angle of 2 degrees–3 degrees and a valgus femoral cut of 7 degrees–9 degrees. Resecting at these respective angles assures that the resected distal femoral condyles lie in a plane which is parallel to the resected proximal tibial surface when the knee is in extension.

The procedures used to balance the knee in the flexion position are more difficult and less accurate than the procedures for balancing in the extension position. In order to balance the knee in flexion, the posterior femoral condyles must be resected so that they lie in a plane which is parallel to the resected proximal tibial surface when the knee is in flexion and the surrounding soft tissues are in balance. Some presently used procedures include referencing the angle of the posterior condylar resection to the classical or anatomic alignment modes used in extension balancing, resecting the condyles parallel to the epicondylar axis, or parallel to the posterior condylar axis.

The angle of resection is measured relative to the center of the two condyles using a jig which has two posterior skids which are placed under the posterior condyles and which orients the jig at 0 degrees rotation relative to the coronal plane of the femur. Drill holes in the jig (or drill bushings attached to the jig) reference an angle of rotation of the femur. The drill holes are used to drill into the resected distal end of the femur so that a cutting block may be attached at a selected angle for resecting the posterior condyles.

None of these procedures accounts for the presence of soft tissues and ligamentous structures. The presence of these tissues and structures tends to negate the assumed correlation between extension balancing and flexion balancing. In particular, the posterior capsule and surrounding soft tissues, which are taut when the knee is in extension, collapse or become laxed when the knee is in flexion and therefore have more significant impact on flexion balance. While the amount of error in flexion balancing due to the presence of these tissues and structures may only amount to a few degrees, it is enough to result in a significant imbalance in the prosthetic knee.

In order to accurately assess the impact of soft tissues on the balance of the knee in flexion, it is necessary to tension the tissues. Several tensioning devices are known in the art which allow the surgeon to spread the femur and tibia apart so that the collateral ligaments may be inspected when the knee is in flexion. Generally, it is found that the medial ligaments are either shorter or have greater tensile strength than the lateral ligaments which results in a valgus rotation of the femur. Most of the known tensioning devices do not provide any means for measuring the degree of rotation and this determination is made with the surgeon's own senses. If it appears that there is a valgus rotation of more than 3 degrees, the surgeon may elect to partially release the medial ligaments which tends to lessen the amount of rotation. If it appears that the amount of rotation is less equal to or less than three degrees, the ligaments are generally left untouched. If it appears that the amount of rotation, according to the indicia, is in a negative range (less than 0 degrees) the surgeon may elect to release the lateral soft tissues until the femur is in an acceptable range of internal rotation (0 to 3 degrees) In any case, the posterior condyles are then resected using a drill jig and cutting block as described above.

U.S. Pat. No. 5,468,244 to Attfield et al. discloses a tensioning device which includes a means for measuring the amount of femoral rotation when the knee is in flexion with the ligaments tensioned. Generally, the device has a tibial engaging plate and a pivoting femoral engaging plate. The plates are arranged between the tibial plateau and the posterior condyles of the femur. The plates are displaced relative to each other and the femoral engaging plate rotates about a central axis in response to femoral rotation. A scale is provided to indicate the angle of rotation of the femoral engaging plate.

The Attfield et al. device is useful in assessing the amount of femoral rotation, but it is not entirely accurate. In particular, the instrument is imprecise because it measures femoral rotation about an axis which lies between the medial and lateral condyles. In reality, the internal (valgus) rotation of the femur is not about a centrally located axis, but is about an axis closer to the medial condylar compartment. In addition, the device provides no assistance in mounting or choosing a cutting block for posterior condyle resection.

SUMMARY OF THE INVENTION

It is therefore an object of the invention to provide an apparatus for accurately balancing a knee in flexion prior to the installation of a prosthetic knee.

It is also an object of the invention to provide an apparatus for determining the degree of femoral rotation when a knee is in flexion.

It is another object of the invention to provide an apparatus for accurately locating a cutting block for resection of the medial and lateral posterior femoral condyles.

It is still another object of the invention to provide methods for determining the degree of femoral rotation when a knee is in flexion and for accurately locating a cutting block for resection of the medial and lateral posterior femoral condyles.

In accord with these objects which will be discussed in detail below, the apparatus of the present invention includes a tibia engaging plate which is coupled to an upstanding rack member, a drill bushing bracket coupled to the rack member by a lockable pinion member, and a femoral positioning jig which is rotatably coupled to the drill bushing bracket. The drill bushing bracket has a pair of spaced apart drill bushings which are dimensionally located to correspond in position to medial and lateral condyles of the femur. The centers of the drill bushings lie in a plane which is parallel to the plane in which the tibia engaging plate lies. The femoral positioning jig is provided with a pair of posterior skids, one for the lateral posterior condyle and one for the medial posterior condyle, a pair of holes for attaching the jig to the resected distal femur with spikes, and a pair of holes for receiving the two drill bushings.

In accord with the invention, two different femoral positioning jigs are provided, one for the right knee and one for the left knee. In both jigs, the hole for receiving the medial drill bushing is circular and the hole for receiving the lateral drill bushing is oblong (deemed to include radially) or kidney shaped. This allows the positioning jig (and the femur) to rotate about the axis of the medial drill bushing. The positioning jigs are also each provided with angular indicia adjacent the lateral oblong hole and the drill bushing bracket is provided with left and right indicia indicating the axial center of each drill bushing.

A method of using the present invention includes the following steps. After the proximal tibia and distal femur are resected in a conventional manner, the knee is moved to the flexion position and the femoral positioning jig is attached to the distal end of the femur in the same manner that a conventional drill jig is now used (i.e. with the posterior skids located under the posterior condyles).

When the jig is in position on the femur, it is secured in place with spikes which are placed through the spike holes in the jig. The rack and pinion are adjusted, if necessary, to bring the drill bushing bracket closest to the tibia engaging plate. The tibia engaging plate is placed on the tibial plateau and the drill bushings are inserted into the drill bushing holes on the femoral positioning jig. The pinion is rotated so that the drill bushing bracket is moved away from the tibia engaging plate. This results in the femoral positioning jig and the femur being moved away from the tibial plateau and a tensioning of the collateral ligaments.

If the medial ligament is shorter or tighter than the lateral ligament, the femur will rotate in the internal (valgus) direction about the medial drill bushing when the collateral ligaments are fully tensioned. The angle of rotation will be indicated on the scale adjacent the oblong hole in the femoral positioning jig. If the angle is greater than 3 degrees, the surgeon may elect to remove some of the medial collateral ligaments to lessen the degree of internal (valgus) rotation.

With the apparatus in this position relative to the tibia and femur, the axes of the drill bushings still define a line which is parallel to the tibial plane. The surgeon now drills two holes in the distal femur, one being drilled through the medial drill bushing and the other being drilled through the lateral drill bushing. The pinion member is then adjusted to remove tension from the ligaments and the device is removed from the knee. The distal end of the femur now has two holes in it and the axes of these holes define a line which is parallel to the tibial plateau when the ligaments are taut. These holes are now used to attach a cutting block which will result in a precise resection of the posterior femoral condyles relative to the resected tibial plateau.

Additional objects and advantages of the invention will become apparent to those skilled in the art upon reference to the detailed description taken in conjunction with the provided figures.

BRIEF DESCRIPTION OF THE DRAWINGS

FIG. 7 is a side elevational view of an apparatus according to the invention with a left femoral positioning jig installed and shown in a position of zero degrees rotation; and FIG. 8 is a view similar to FIG. 7 with the jig shown in a position of five degrees internal (valgus) rotation.

DETAILED DESCRIPTION OF THE PREFERRED EMBODIMENTS

Figure 1:
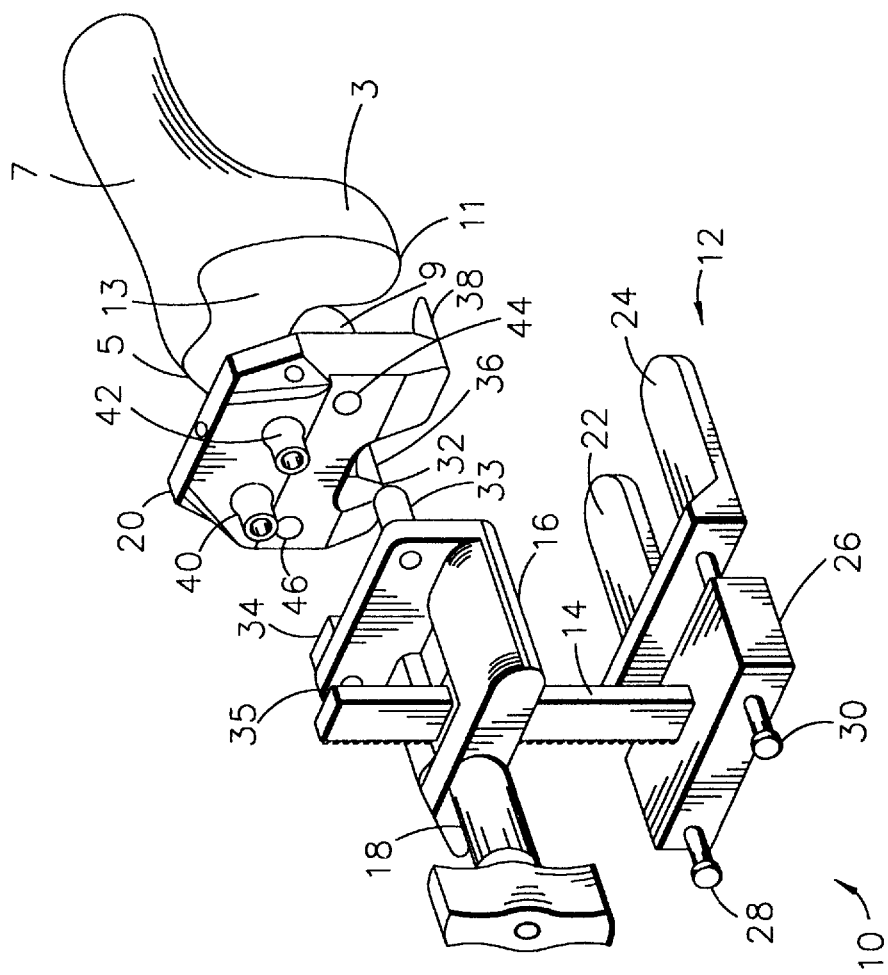
FIG. 1 is an exploded perspective view of an apparatus according to the invention shown adjacent to a resected femur.
Figures 2, 3:
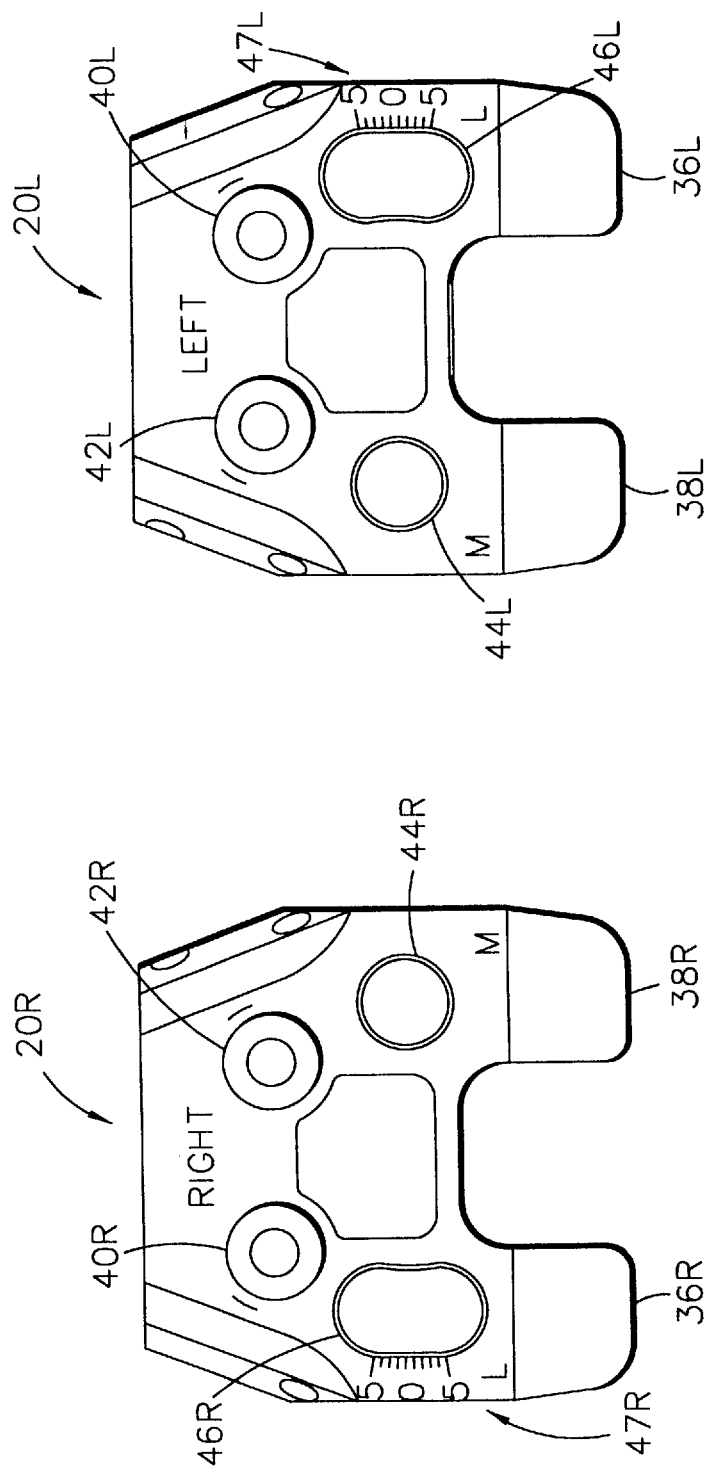
FIG. 2 is a side elevational view of a right knee femoral positioning jig.
FIG. 3 is a side elevational view of a left knee femoral positioning jig.

Referring now to FIGS. 1 through 3, the apparatus 10 of the present invention includes a tibia engaging plate 12 which is coupled to an upstanding rack member 14, a drill bushing bracket 16 coupled to the rack member 14 by a lockable pinion member 18, and a femoral positioning jig 20 which is rotatably coupled to the drill bushing bracket 16. The tibia engaging plate 12 has a pair of posterior skids 22, 24 and is coupled to the rack member base plate 26 by a pair of anterior-posterior positioning rods 28, 30 which permit anterior-posterior movement of the skids 22, 24 relative to the rack member 14. The drill bushing bracket 16 has a pair of spaced apart posterior drill bushings 32, 34 which are dimensionally located to correspond in position to medial and lateral condyles 3, 5 of the femur 7. The centers of the drill bushings 32, 34 lie in a plane which is parallel to the plane in which the skids 22, 24 of the tibia engaging plate 12 lies.

The bushing bracket 16 is also provided (preferably inscribed) with two zero degree reference marks 33, 35 which also lie in the same plane as the centers of the bushings 32, 34. The femoral positioning jig 20 is provided with a pair of posterior skids 36, 38, one for the lateral posterior condyle 9 and one for the medial posterior condyle 11, a pair of holes 40, 42 (preferably anterior bushings) for attaching the jig 20 to the resected distal femur 13 with spikes, and a pair of holes 44, 46 for receiving the two posterior drill bushings 32, 34.

According to one aspect of the invention, the lateral hole 46 is oblong or kidney shaped and angle indicia 47 are provided on the jig on the lateral side of the lateral hole as described in more detail below.

In accord with the invention, and as shown in FIGS. 2 and 3, two different femoral positioning jigs 20R, 20L (referred to generally as 20) are provided, one for the right knee and one for the left knee (where right and left are as viewed by the patient). Both jigs are substantially the same but for the relative locations of the holes 44 and 46.

As shown in FIG. 2, the circular hole 44R of the right jig 20R is on the right side of the jig 20R as viewed by the surgeon and the oblong hole 46R is on the left side of the jig 20R as viewed by the surgeon. As shown in FIG. 3, the circular hole 44L of the left jig 20L is on the left side of the jig 20L as viewed by the surgeon and the oblong hole 46L is on the right side of the jig 20L as viewed by the surgeon. Angle indicia 47R, 47L are provided (preferably inscribed) on the portion of the jig 20R, 20L immediately lateral to the lateral oblong (or kidney shaped) hole 46R, 46L. The jigs 20R, 20L are individually attachable to (and removable from) the bushing bracket 16 by sliding the jig onto the bracket 16 such that the posterior drill bushings 32, 34 extend into the holes 44, 46.

Referring now to FIGS. 1 and 4–8, a method of using the apparatus 10 includes the following steps. After the proximal tibia 15 and distal femur 7 are resected in a conventional manner, the knee is moved to the flexion position and the femoral positioning jig (20A or 20B, referred to generally as 20) is placed against the distal end 13 of the femur 7 with the posterior skids 36, 38 located under the posterior condyles 9, 11.

Figure 4:
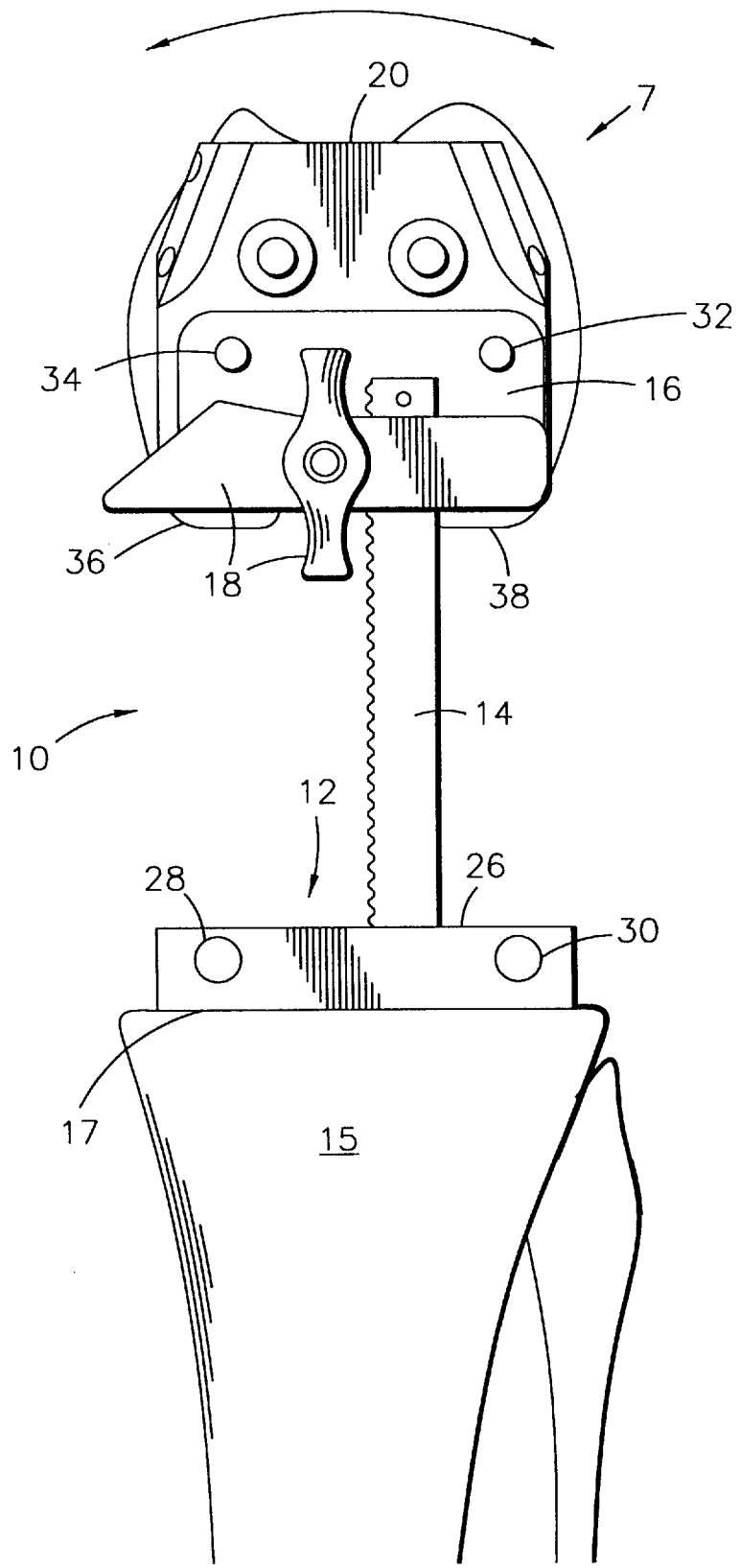
FIG. 4 is a schematic side elevational view of an apparatus according to the invention coupled to a femur and tibia in a position to apply tension to soft tissues.

When the jig is in position on the femur, it is secured in place with spikes (not shown) which are placed through the spike holes (anterior bushings) 40, 42 in the jig. The rack 14 and locking pinion 18 are adjusted, if necessary, to bring the drill bushing bracket 16 closest to the tibia engaging plate 12. The tibia engaging plate 12 is placed on the tibial plateau 17 and the drill bushings 32, 34 are inserted into the drill bushing holes 44, 46 on the femoral positioning jig 20. The locking pinion 18 is rotated so that the drill bushing bracket 16 is moved away from the tibia engaging plate 12 as shown in FIG. 4. This results in the femoral positioning jig 20 and the femur 7 being moved away from the tibial plateau 17 and a tensioning of the collateral ligaments (not shown).

Figure 6:
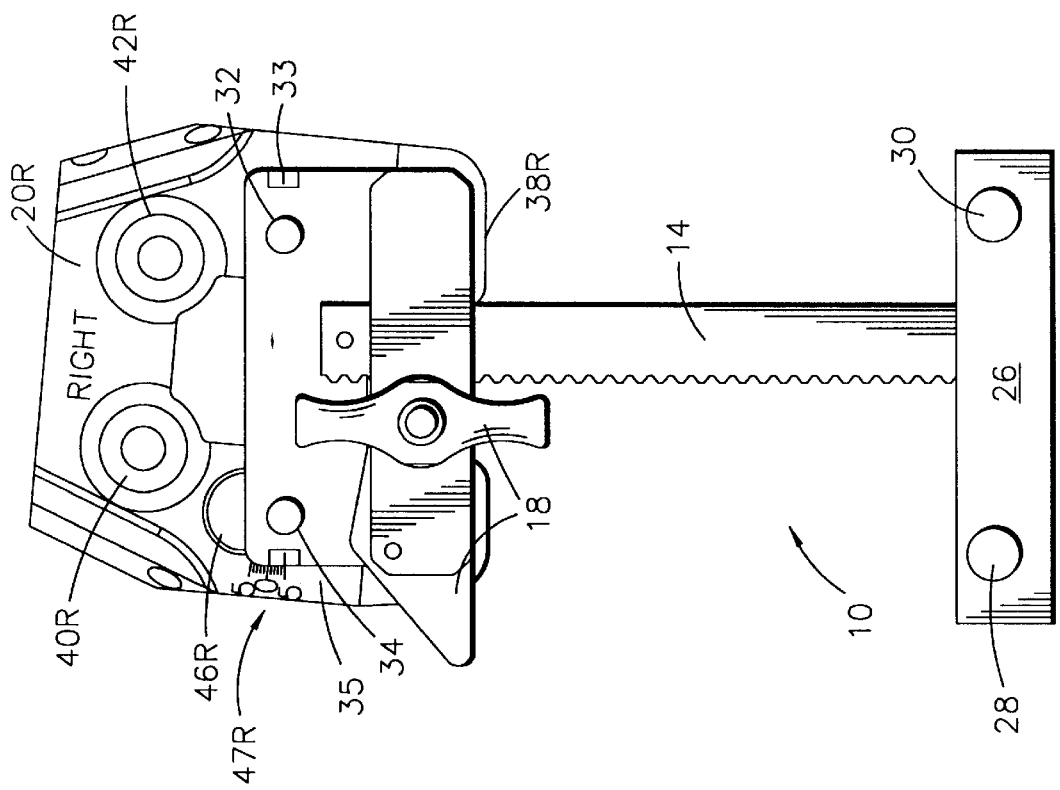
FIG. 6 is a view similar to FIG. 5 with the jig shown in a position of five degrees internal (valgus) rotation.
Figure 5:
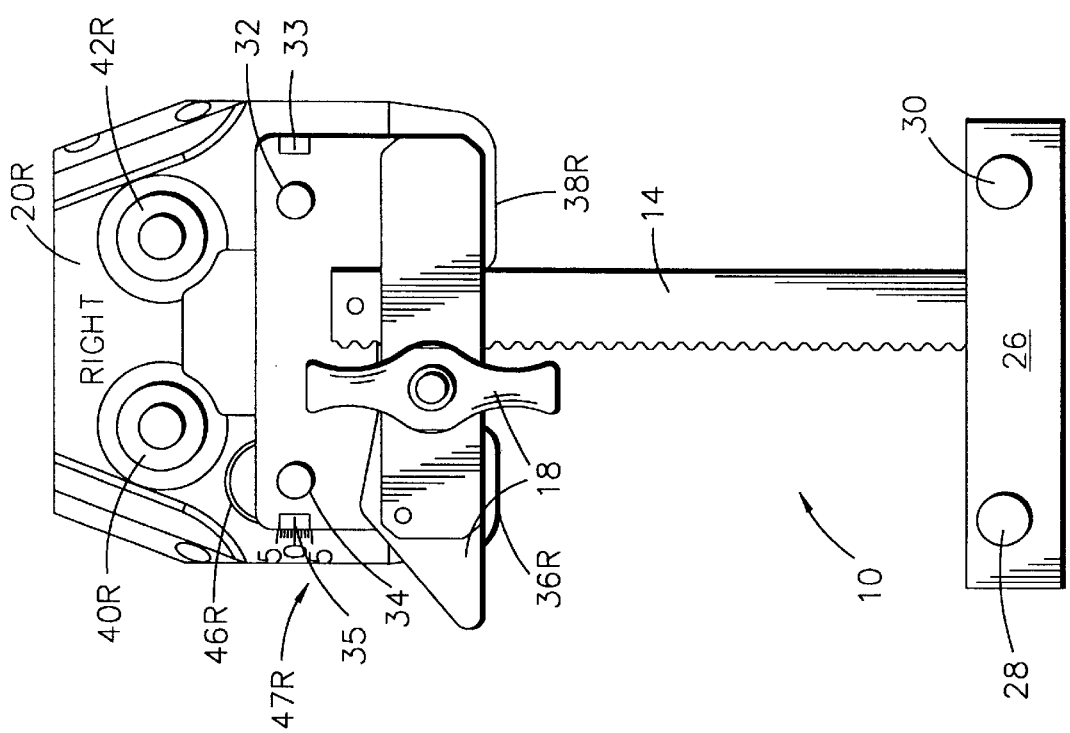
FIG. 5 is a side elevational view of an apparatus according to the invention with a right femoral positioning jig installed and shown in a position of zero degrees rotation.

If the collateral ligaments are of equal length and strength, the femur will not rotate and the positioning jig 20 will assume the position shown in FIG. 5 for the right knee or FIG. 7 for the left knee. If the medial ligament is shorter or tighter than the lateral ligament, the femur 7 and the positioning jig 20 will rotate in the internal (valgus) direction about the medial drill bushing (32 for the right leg, 34 for the left leg) when the ligaments are fully tensioned. The angle of rotation will be indicated on the scale 47 adjacent the oblong hole 46 in the femoral positioning jig 20 as shown in FIGS. 6 and 8.

If the angle is greater than 3 degrees, the surgeon may elect to remove some of the medial collateral ligaments to lessen the degree of rotation. With the apparatus 10 in this position relative to the tibia 15 and the femur 7, the axes of the drill bushings 32, 34 still define a line which is parallel to the tibial plateau 17. Therefore, after removing ligaments (if necessary), the surgeon drills two holes in the distal femur 13, one being drilled through each drill bushing 32, 34. The locking pinion member 18 is then unlocked to remove tension from the ligaments and the apparatus 10 is removed from the knee. The distal end 13 of the femur 7 now has two holes in it and the axes of these holes define a line which is parallel to the tibial plateau 17 when the ligaments are taut. These holes are now used to attach a cutting block which will result in a precise resection of the posterior femoral condyles relative 9, 11 to the resected tibial plateau 17.

There have been described and illustrated herein a surgical apparatus for use in total knee arthroplasty and a surgical method for using the apparatus. While particular embodiments of the invention have been described, it is not intended that the invention be limited thereto, as it is intended that the invention be as broad in scope as the art will allow and that the specification be read likewise.

For example, while the apparatus has been shown and described with two different removable positioning jigs, it is within the scope of the invention to provide separate apparatus for left and right legs where the left and right positioning jigs are not removable from the respective apparatus. In addition, while the tibia engaging plate has been shown with two posterior skids, more or fewer skids can achieve substantially the same results. Also, while the apparatus has been shown and described as having a rack and pinion arrangement for moving the drill bushing bracket relative to the tibia engaging plate, it will be appreciated that other designs could achieve the same results in substantially the same way.

Furthermore, while the femoral positioning jig has been shown as having a particular shape with particular locations for the spike holes, it will be understood that a positioning jig having a different shape can achieve the same results and that different means for securing the jig to the femur can also achieve the same results. It will therefore be appreciated by those skilled in the art that yet other modifications could be made to the provided invention without deviating from its spirit and scope as so claimed.

What is claimed is:

1. A surgical apparatus for tensioning soft tissues between the femur and the tibia during knee arthroplasty, comprising:

(a) first engaging means for engaging a tibial plateau;

(b) second engaging means for engaging medial and lateral femoral condyles, said second engaging means having a medial side, a central region and a lateral side;

(c) translation means coupled to said first and second engaging means for translationally moving said first and second engagement means relative to each other; and (d) medial rotational coupling means for coupling said second engaging means to said translation means such that said second engaging means is free to rotate relative to said translation means about a point which is laterally offset from said central region toward said medial side, so that rotation is substantially aligned with the medial femoral condyle.

2. A surgical apparatus according to claim 1, further comprising angle indication means for indicating an angle of rotation of said second engaging means.

3. A surgical apparatus according to claim 1, further comprising locating means coupled to said translation means for locating at least two points on the femur such that the two points define a line which is substantially parallel to the tibial plateau.

4. A surgical apparatus according to claim 3, wherein said locating means includes a pair of spaced apart drill bushings.

5. A surgical apparatus according to claim 1, wherein said second engaging means includes means for securing said second engaging means to the femur.

6. A surgical apparatus according to claim 5, wherein said means for securing includes a pair of spaced apart spike holes.

7. A surgical apparatus according to claim 1, further comprising anterior-posterior positioning means for anterior posterior positioning of said first engaging means relative to said second engaging means.

8. A surgical apparatus for tensioning soft tissues between the femur and the tibia during knee arthroplasty, comprising:

(a) tibial engagement means for engaging a resected tibial plateau;

(b) a drill bushing bracket having a lateral drill bushing and a medial drill bushing, each drill bushing having an axis, said axes of said pair of drill bushings defining a first plane;

(c) translation means coupled to said tibial engagement means and said drill bushing bracket for translationally moving said drill bushing bracket relative to said tibial engagement means; and (d) a femoral positioning jig rotationally coupled to said medial drill bushing, said femoral positioning jig having a posterior medial condyle engaging skid, a posterior lateral condyle engaging skid, and means for securing the position of said jig relative to the femur, wherein said first plane remains substantially parallel to the resected tibial plateau when said tibial engagement means engages the plateau, and said positioning jig and the femur are free to rotate about said medial drill bushing when said positioning jig is secured to the femur.

9. A surgical apparatus according to claim 8, further comprising angle indicia for indicating an angle of rotation of the femur about said medial drill bushing.

10. A surgical apparatus according to claim 9, wherein said angle indicia includes indicia on a lateral portion of said drill bushing bracket and indicia on a lateral portion of said positioning jig.

11. A surgical apparatus according to claim 9, wherein said translation means includes a rack and pinion.

12. A surgical apparatus according to claim 8, wherein said positioning jig has a substantially circular medial hole for receiving said medial drill bushing and a substantially oblong lateral hole for receiving said lateral drill bushing, such that said rotational coupling of said positioning jig is effected by inserting said medial drill bushing into said medial hole and said lateral drill bushing into said lateral hole.

13. A surgical apparatus according to claim 12, wherein said positioning jig is removably coupled to said medial drill bushing.

14. A surgical apparatus according to claim 13, further comprising separate left and right positioning jigs, said left positioning jig for use with a left leg and said right positioning jig for use with a right leg.

15. A surgical apparatus according to claim 8, wherein said tibia engagement means includes a lateral posterior skid and a medial posterior skid.

16. A surgical apparatus according to claim 8, wherein said means for securing the position of said jig relative to the femur includes a pair of spike holes in said positioning jig.

17. A method for tensioning a knee in flexion during knee arthroplasty, comprising the steps of:

(a) resecting a portion of the proximal tibia and a portion of the distal femur;

(b) moving the knee to the flexion position;

(c) attaching a femoral positioning jig to the distal end of the femur, the femoral positioning jig having a medial rotation coupling;

(d) placing a first end of a tensioning device on the tibial plateau and rotationally coupling a second end of the tensioning device to the medial rotation coupling of the femoral positioning jig, the second end of the tensioning device having locating structure for locating a line on the femur which is parallel to the tibial plateau; and (e) adjusting the tensioning device to move the femur and tibia apart from each other such that collateral ligaments are tensioned.

18. A method according to claim 17, wherein the femoral positioning jig has a posterior medial condyle engaging skid, a posterior lateral condyle engaging skid, and said step of attaching includes positioning the skids under the posterior condyles.

19. A method according to claim 17 and further for balancing a knee in flexion during knee arthroplasty, said method further comprising the steps of:

(a) determining rotation of the positioning jig about the medial rotation coupling; and (b) removing a portion of the collateral ligaments to lessen the degree of rotation, if necessary, based on said step of determining.

20. A method according to claim 19 and further for resecting the posterior condyles in a plane substantially parallel to the tibial plateau when soft tissues are tensioned, further comprising the steps of:

(a) using the locating structure, marking the distal end of the femur in at least two points which define a line which is parallel to the tibial plateau when the collateral ligaments are tensioned;

(b) removing the tensioning device and the positioning jig;

(c) aligning a cutting block with the markings on the distal end of the femur and securing it to the femur; and (d) resecting the posterior condyles using the cutting block as a guide.

21. A method according to claim 17 and further for resecting the posterior condyles in a plane substantially parallel to the tibial plateau when soft tissues are tensioned, further comprising the steps of:

(a) using the locating structure, marking the distal end of the femur in at least two points which define a line which is parallel to the tibial plateau when the collateral ligaments are tensioned;
(b) removing the tensioning device and the positioning jig;
(c) aligning a cutting block with the markings on the distal end of the femur and securing it to the femur; and
(d) resecting the posterior condyles using the cutting block as a guide.

22. A method according to claim 21, wherein said locating structure includes a pair of drill bushings, and said step of marking includes drilling a pair of holes using the drill bushings as guides.

* * * * *